(12) United States Patent  
Rushbrook et al.

(10) Patent No.: US 6,740,865 B1  
(45) Date of Patent: May 25, 2004

(54) IMAGING SYSTEM FOR LUMINESCENCE ASSAYS

(75) Inventors: John Gordon Rushbrook, Cambridge (GB); Claire Elizabeth Hooper, Cambridge (GB)

(73) Assignee: Packard Instrument Company, Inc., Meriden, CT (US)

( * ) Notice: Subject to any disclaimer, the term of this patent is extended or adjusted under 35 U.S.C. 154(b) by 0 days.

(21) Appl. No.: 09/743,132

(22) PCT Filed: Jul. 20, 1999

(86) PCT No.: PCT/GB99/02348  
§ 371 (c)(1),  
(2), (4) Date: Jan. 3, 2001

(87) PCT Pub. No.: WO00/05569  
PCT Pub. Date: Feb. 3, 2000

(30) Foreign Application Priority Data

Jul. 21, 1998 (GB) .............................................. 9815702

(51) Int. Cl.$^7$ ................................................. G01I 3/00
(52) U.S. Cl. .............................. 250/227.14; 250/227.11; 356/319
(58) Field of Search ....................... 250/227.2, 227.11, 250/227.14, 227.18, 227.26, 461.1; 385/115, 116, 120; 356/320, 319, 318; 204/452

(56) References Cited

U.S. PATENT DOCUMENTS 5,862,285 A * 1/1999 Danielian et al. ............ 385/121

FOREIGN PATENT DOCUMENTS

EP 0266881 * 11/1988

* cited by examiner

Primary Examiner—David V. Bruce  
Assistant Examiner—Hoon Song  
(74) Attorney, Agent, or Firm—Barnes & Thornburg (57) ABSTRACT

Apparatus for detecting light emitted by assay samples is provided, in which light emitted by the sample is collected for transmission to a charge coupled device camera (74) by an optical fiber bundle. The cross-sectional area of the optical fiber bundle corresponds to the area of the sample, the end of which is located close to the sample for detecting any light emitted therefrom, and selected fibers (30) of those making up the bundle are separated from the remainder and extend to a source of excitation radiation (76) and serve to convey excitation radiation (if required) directly to a corresponding plurality of points distributed over the are of the end face of the bundle and therefore over the area of the sample. The remaining fibers (32, 38) of the bundle serve to collect emitted light (whether generated by fluorescence caused by excitation or otherwise) and provide a light path to the change coupled device camera, wherein the ends of the excitation fibers and the ends of the emitted light collecting fibers area distributed uniformly over the area of the fiber bundle presented to the reaction site.

18 Claims, 2 Drawing Sheets

96 holes
spacing - 3.9mm
in circle - 75mm diam.

Fig. 2

192 holes diam - 2.0mm
spacing - 1.9mm
within 27 x 27mm
area of camera

Fig. 3

Fig. 4

IMAGING SYSTEM FOR LUMINESCENCE ASSAYS

FIELD OF INVENTION

This invention concerns methods and apparatus for imaging, and particularly the imaging of luminescence samples of the type in which the sample is illuminated with excitation radiation such as ultra-violet light, or where the sample is activated by some suitable chemiluminescent or bioluminescent means, and is interrogated for any resulting emission light due for example to fluorescence within the sample. The invention is particularly concerned with multipath (or multichannel) systems in which a large number of samples can emit light and need to be interrogated at the same time.

BACKGROUND TO THE INVENTION

PCT Application No. WO 98/0144 describes a fluorescence assay imaging system in which excitation radiation is supplied to the assay sample via an annular sleeve fitted around the end of a fibre optic bundle the end of which is in close proximity to the assay sample. The fibres collect emitted light due to fluorescence induced by the excitation radiation. It has been found that using an annular source of radiation does not produce the most uniform and sufficiently intense illumination of the assay reaction site, fan it is an object of the present invention to improve the uniformity and intensity of excitation illumination over the p resented area of each assay reaction site, without prejudicing any light collecting efficiency of the fibres.

Achieving uniformity over the reaction site has been found to be even more difficult to achieve where the sample is a very thin layer of cells or is contained or upon a thin gel or membrane.

The problems identified above become even greater as the area of each reaction site decreases. This is tending to occur as greater numbers of samples and therefore reaction sites, are accommodated in a sample supporting device such as a multi-well plate, multi-site membrane or gel or wafer, or chip of silicon or like material.

The invention endeavours to provide an improved illumination and collection system which allows sufficient excitation radiation to be introduced if required by the assay, and emitted light to be collected from reaction sites such as those in a 96 well plate for which the earlier imaging system of Wo 98/01744 is generally adequate, as well as the much smaller reaction sites such as now exist in high format multiple sample plates.

The invention is applicable to any luminescence producing assay.

Light emitting luminescence processes, including fluorescence, chemiluminescence and bioluminescence, and/or a combination of these processes, can be used in the measurements of biomedical and chemical assays. The wavelengths of excitation and emission for these processes are characteristic of the fluorescent and/or luminescent molecules and moieties being used. Wavelength ranges used are in the UV, visible, red and infra-red parts of the spectrum. A typical excitation range is 260–800 nm, a typical emission range is 320–1100 nm.

In the present application, the luminescent processes being measured include fluorescence, chemi- and bioluminescence.

In normal fluorescence, a fluorescent molecule or flurophore is excited by external radiation, such that it absorbs light energy and re-emits light at a longer wavelength.

The fluorescence may occur almost immediately, or later in time in which event it is referred to as time-delayed fluorescence.

In an alternative luminescent process, involving what is generally known as fluorescence or chemiluminescence energy transfer, energy is transferred from a donor molecule or moiety to an acceptor molecule or moiety, via a non-radiative mechanism. This mechanism can occur, eg via resonance or via electron transfer between atoms and molecules. Such luminescent donor and acceptor molecules may be fluorescent or chemi- or bioluminescent. The donor or acceptor molecules are generally different, and more than one molecule type may be used in either the donor or acceptor stage of the process.

The activation of the donor molecules may be via excitation light in the case of fluorescence or via chemical activation in the case of chemi- or bioluminescence. With fluorescence activation there may be a short delay between the excitation of the donor and the emission of the acceptor, in the range microseconds to milliseconds.

Energy transfer only takes place over very short distances (typically 10 nm and therefore the donor and acceptor molecules need to be in very close proximity. This can be achieved by direct bonding (eg covalent) of the donor and acceptor molecules, or linking of the two molecules by a biochemical bridge (eg via a peptide link). Alternatively, the molecules may be coated or bonded onto a solid phase, such that they are in close proximity (eg a microplate or bead). In a further example, the energy transfer from the donor may be via a reactive intermediate product, eg singlet oxygen or some excited chemical radical, which diffuses, eg in a fluid, to interact with the acceptor molecule.

Where no energy transfer takes place between the donor and the acceptor molecules, the donor molecule itself, when activated, will release energy directly as light, with emission wavelength characteristic of that molecule itself. When energy transfer occurs, the emission wavelength is characteristic of the acceptor molecule. Where the donor and acceptor molecules are different, the light emission from the acceptor molecules may be of a longer or shorter wavelength to the emission characteristic of the donor molecule.

When used in biomedical or chemical assays, to measure the presence or activity of a compound or agent, these luminescent processes may be used as an indicator of the presence or activity of such a compound or agent. The increase or decrease in light emission, from the donor or acceptor molecules, may be used as an indicator of the unknown compound being assayed. For example, the unknown compound might interact directly or indirectly with the energy transfer process, eg break the bridge between the donor and acceptor molecules or otherwise inhibit the transfer process. This would result in a change in the relative intensity of light emission of the donor and acceptor molecules, which could be detected by measurement, for example, at the two or more wavelengths which are characteristic of each molecule. Thus a ratiometric measurement involving various pairs of wavelengths characteristic of the molecules used may be appropriate.

PRIOR ART

EP 0580362 A1 describes a fluorescence detecting apparatus in which some of the fibres terminating below a sealed sample holder 7 convey excitation radiation to the sample, and others convey the fluorescence radiation away to a detector. On pages 3 and 4, a preferred arrangement for weak fluorescence is described, in which the excitation fibres are concentrated in the centre of the bundle presented to the sample and those for receiving and conveying away from the fluorescence radiation are located annularly around the central excitation fibre core.

It was no doubt thought that by concentrating the excitation radiation fibres into a central region of the sample, and collating the weak emitted fluorescence from an annular region of the central core, much of the unwanted excitation radiation reflected or refracted back towards the fibres by the sample (or the reaction site), would thereby not be collected by the fibres leading to the detector.

However it has been found that this creates a virtual dead region in the centre of the reaction site where the product of excitation and light collection for any point is very low or zero (due to the annular arrangement of the collecting fibres), and genuine signals cannot be distinguished from background noise emanating from a large central area of the reaction site.

The present invention seeks to overcome this problem since for reliable and accurate assay evaluation, not only is it Li necessary for good uniformity of response to exist between one well and another over the entire well plate, but it is also very important that there is a high degree of uniformity of response across the area of each assay reaction site so that if the latter can be considered to be divided into a large number of tiny adjacent areas the product of excitation incident on and light collection from each of those tiny areas should be substantially the same over the whole area of the assay.

SUMMARY OF THE INVENTION

According to the present invention, there is provided apparatus for detecting luminescence in a sample, in which light emitted by the sample is collected for transmission to photosensitive detector means by an optical fibre bundle the cross-sectional area of which corresponds to the area of the sample and one end of which is located close to but spaced from the sample for directly illuminating the sample and collecting light emitted therefrom, selected ones of the fibres making up the bundle are separated from the remainder and extend to a light source to convey the light for direct illumination of the sample, and other fibres of the bundle serve to collect light emitted from the sample due to luninescence and provide a light path therefor to the photosensitive detector means, wherein the light collecting fibres are divided into a plurality of groups for conveying light to different regions of the detector meqns, thereby providing parallel light paths from the sample to the detector, and a wavelength selective filter is located in each of the said light paths to permit only selected wavelengths of light to reach the region of the detector means associated with each light path, and wherein the fibres in the bundle are arranged in a symmetrical pattern 80 that in the end face of the bundle presented to the sample, each sample illuninating fibre is surrounded by a ring of six light collecting fibres which, around the ring, successively constitute fibres appertaining to the respective groups of said light collecting fibres, whereby the sample illuminating fibres and the light collecting fibres are distributed uniformly over the area of the fibre bundle presented to the sample.

The detector may comprise a CCD array, a cooled CCD camera, an intensified CCD (ICCD) array, or an array of photodiodes or PMT's, or a or similar device.

Preferably the filters are interference filters.

In the preferred arrangement one third of the fibres in the bundle can convey light radiation to the sample, another third of the fibres collect and convey emitted radiation via a first wavelength selective filter to a first region of the photosensitive detector, and the remaining third of the fibres collect and convey emitted radiation via a second wavelength selective filter to a second region of the detector. Except for peripheral regions of the fibre bundle area, each emission collecting fibre will be a member of each of three separate but intersecting rings of emission collecting fibres, centered on three light conveying fibres which are immediate neighbours of one another.

By distributing the light conveying fibres uniformly over the end of the bundle presented to the sample, and likewise distributing the emission collecting fibres in a similar uniform manner, there is a greater chance that light transmitted to the sample will penetrate to sites in the sample which are capable on stimulation/excitation of emitting light, and there is also a good chance that the very small quantities of light emitted in response to such stimulation or excitation will be collected by emission collecting fibres and conveyed to the photosensitive detector.

Typically the samples are contained in small wells arranged in a matrix in a plate known as a well plate, at least one end of each of the wells being closed so as to retain a liquid sample therein, but in which the closed end is transparent and forms a window to enable light to penetrate into the sample to excite the latter and not to impede light emitted from the sample due to fluorescence or energy transfer, from passing in the return direction therethrough.

Assay analysis often involves studying reactions which have occurred in hundreds or thousands of samples and it is commonplace for well plates to be constructed having a matrix of some many hundreds or thousands of wells. One typical well plate contains 3456 wells which is conveniently interrogated by investigating the luminescence from 96 wells at a time using a presentation plate which aligns 96 fibre bundles with 96 of the 3456 wells in the well plate, and stepping the presentation plate 36 times relative to the well plate so as to interrogate all 3456 wells.

In the case of a 3456 well plate having circular wells, typically each well has a diameter of 1mm. In the case of a well plate having a smaller number of wells, each well can be larger. The wells can in fact be of any cross-sectional shape but normally are circular or square.

According to a preferred feature of the invention the two groups of emission gathering fibres from each of the 96 bundles are collated into two collections each of 96 bundles, and each of the two collections is presented to one of two wavelength selective interference filters, each of which has a different wavelength filtering characteristic from the other, and two further bundles of optical fibres downstream of the filters separately collect and transfer light which is transmitted by the two filters, to two discrete regions of the detector.

The collections of fibres are preferably re-arranged as required so as to optimally utilise the area of the filter, and fibres leading from the filters to the detector are preferably re-arranged, if required, so as to optimally occupy the active area of the detector.

In general this will entail re-arranging the downstream fibres so as to conform to the aspect ratio of the detector if the latter is different from the aspect ratio of the filter.

Thus in the case of a square detector, the fibres leading from the interference filter are preferably re-arranged in two rectangular arrays which when arranged side by side make up a square corresponding to the square proportions of the detector.

Although rearrangement of the fibre bundles occurs, by maintaining fixed registration between the 192 fibre bundle ends presented to the detector with the 192 fibre bundles derived from the 96 well inspecting bundles, the presence of emitted light from any one well can be determined by interrogating the X,Y coordinate positions in the detector array corresponding to the images of two fibre bundles in the two groups of 96 bundles presented to the detector, which correlate to the two groups of fibres from the fibre bundle inspecting the particular well.

According to a preferred aspect of the invention, each of the fibre optic bundles presented to each well site, is made up of 45 Ge-doped silica clad, silica fibres, each typically of a diameter of 100–200 microns, 15 of which are separated out as a sub-bundle and combined with similar sub-bundles from each of the other 96 bundles, and which extend to a source of excitation radiation such as UV light. One or more filters may be located between the UV source and the sub-bundles. The remaining 30 fibres from each of the 96 bundles are divided into two further sub-bundles each of 15 fibres. This produces a total of 192 emission collecting sub-bundles, 96 of which lead to discreet positions at the input of a first interference filter, and the other 96 of which lead to discreet positions at the input of a second interference filter, which transmits different wavelengths from those transmitted by the first filter.

Light transmitted by the interference filters, enters one or the other of two downstream groups of 96 sub-bundles arranged on a one to one basis with each of the two arrangements of 96 sub-bundles upstream of the filters, and the downstream sub bundles are merged to form an array of 192 sub-bundles having the same aspect ratio as that of the detector.

Where the aspect ratio of the detector is approximately square, the 192 sub-bundles are conveniently arranged into 14 rows, the first and last of which contain 12 sub-bundles and with each of the intermediate 12 rows, containing 14 sub-bundles. The array of rows and columns thereby defines what is essentially a square area with each of the corners missing, for presentation to a generally square aspect ratio detector.

Typically the interference filters are circular and have a diameter of approximately 80 mm.

Typically a square input window of a CCD camera has 27 mm long sides.

The invention also lies in a method of detecting emitted luminescence from an assay sample in which a fibre optic bundle having a cross-sectional area commensurate with the area of the sample is located with one end close to the latter, and fibres which are to collect and transmit emitted light are uniformly distributed over the cross-section of the bundle amongst other fibres in the bundle through which light can be conveyed to the sample, if required.

The method may include the further step of dividing the detected light into two or more channels by arranging that the light collecting fibres are split into two or more sub-bundles of similar numbers of fibres, each sub-bundle serving to convey light to one of a corresponding plurality of interference filters having differing pass bands, causing the filtered light to fall onto differently addressable regions of a photosensitive detector, and comparing the electrical signals from the differently addressable regions to permit a comparison to be made as between the quantity of light transmitted by one of the filters and that transmitted by the other.

PCT Application WO 98/01744 describes an imaging system for light emitting assays in which an interference filter is used to enable highly selective transmission of the radiation which is to reach the imaging device such as a camera.

Whilst an interference filter has a very sharp cut-off and allows virtually 100% transmission of desired wavelengths and virtually zero transmission of unwanted wavelengths, breakthrough can occur if light of a non acceptable wavelength is incident on the filter at a sufficiently large angle to satisfy the transmission criterion for the interference filter, ie the relationship between wavelength and angle of incidence for the interference filter.

By using optical fibres to transmit light from the sample to the interference filter, and shielding the fibre ends from extraneous light as much as possible, rogue rays will in general be restricted to reflected or refracted excitation light and this will in general be of a fixed wavelength. Rays of such light which are capable of being transmitted via the optical fibres and are of such large angle as to be capable of breaking through the interference filter would probably be Skew rays and it has already been proposed to position an angle collimator between the interference filter and the camera to reduce the transfer to the camera of Skew rays issuing from the interference filter.

According to another preferred aspect of the present invention, in apparatus as aforesaid, an additional optical filter is provided in the light path to the detector, preferably between the assay sample and the interference filter, and the characteristics of the additional optical filter are such that light of a wavelength corresponding to that emitted by the sample will be transmitted by the filter but light of a wavelength equivalent to that employed to excite the sample will be strongly attenuated or "blocked" by the filter before reaching the interference filter, irrespective of the angle of incidence of the radiation on the filter.

The additional filter may be located immediately in advance of the interference filter between it and the ends of the optical fibres transmitting light from the assay sample to the interference filter.

A primary purpose of the additional filter is to remove rays of excitation radiation and particularly skew rays of excitation radiation that would otherwise be transmitted through the interference filter and could have a very high intensity at the detector as compared with the intensity of any radiation arising at the detector as a result assay luminescence.

The characteristics of the emission filters required for detection of these types of luminescent processes, especially where the emission wavelengths of the acceptor molecules may be shorter or longer than the wavelengths of the donor molecule, has to be considered.

In the case of fluorescein, which produces normal fluorescence, excitation light of, eg 485 nm produces fluorescent light emitted at longer wavelength, eg 530 nm.

Any excitation light appearing at a 530 nm band pass interference filter, with an angle to the filter satisfying the Fabry-Perot condition, will be transmitted. This is the case, eg for 485 nm light arriving at −54°. In the case of fibre optic components, skew rays can be transmitted and enter the filter at such an angle. A blocking filter is needed to eliminate any light which might be transmitted by virtue of the Fabry-Perot condition, or by punch-through.

In the case of fluorescence energy transfer assays, where the excitation light is used to activate the donor molecules, and is say of wavelength 480 nm, and is of shorter wavelength than the light emitted by the acceptor molecule, eg 540 nm, then the same situation applies. This means that a blocking filter is required to absorb the 480 nm excitation light that would otherwise be transmitted by the Fabry-Perot condition for the interference filter which is chosen to transmit the 540 nm emission light. The blocking filter also helps to eliminate any punch-through of the 480 nm light.

In the case of energy transfer assays where chemi- or bioluminescent activation of the donor molecules occurs, and hence no excitation light is used, there is still the problem arising from the donor or acceptor molecules having different emission wavelengths, and hence the need to detect the longer wavelength in the presence of the shorter wavelength, where the intensity of the shorter wavelength is significantly greater than the intensity of the longer wavelength.

This is particularly the case where the emission wavelength of the acceptor is shorter than the emission wavelength of the donor, and where the energy transfer process has resulted in significant amplification of the signal generated by the acceptor molecules. Again a blocking filter is desirable to prevent light of the shorter wavelength being passed by the interference filter for the longer wavelength light, by virtue of the shorter wavelength light being transmitted through the filter by satisfying the Fabry-Perot condition, or by punch-through.

In a typical example of apparatus embodying the invention, blue is excitation light having a wavelength of 485 nm is employed to excite green fluorescence having a wavelength of the order of 530 nm. Any blue light finding its way down fibres which should only transmit emitted green fluorescence, for example by reflection from the bottom of a sample plate containing the assay, may exit the fibres in a cone of Skew rays of sufficiently large angle to satisfy the transmission criterion of the interference filter, and an intense ring of blue light will be presented to the detector.

Without the presence of the additional filter proposed by the invention, this unwanted light will be conveyed via the remaining fibre optics to the camera. Unless this ring of blue light is eliminated by an angle collimating device ahead of the camera as already proposed, the ring of light will swamp the camera around a region of the camera sensor to which low level green light due to fluorescence will be conveyed if present.

Although an angle collimator will reduce the intensity of such a ring, it is not a complete solution to the problem, and in the presence of strong Skew rays, sufficient swamping can still occur to render green light at the camera virtually indistinguishable from noise etc, and if the assay emits light for example by fluorescence, the small spot of green light attributable to the fluorescence can be surrounded by and essentially swamped by the ring of intense blue light produced by the unwanted breakthrough of excitation radiation even in the presence of an angle collimator. A supplementary filter, as proposed by the invention, fitted ahead of, or downstream of, or both ahead and downstream of the interference filter, reduces this significantly.

In order to reduce Skew ray incidence on the interference filter the additional filter must be located ahead of the interference filter. It may be in contact therewith.

To be effective the additional filter should have a sharp cut-off between transmission and attenuation, and a high attenuation of wavelengths beyond the cut-off point. In the example given above where the blue light wavelength is 485 nm and the emitted radiation due eg to fluorescence, has a wavelength of 530 nm, a filter having a cut-off at 515 nm would be appropriate, thereby transmitting wavelengths of the order of 530 nm but inhibiting wavelengths of the order of 485 nm.

A filter having such a characteristic is a Schott filter, Type OG515. This transmits wavelengths above approximately 515 nm but severely attenuates any wavelengths significantly below 515 nm. Such filters constitute blocking filters.

The use of an additional filter provided by the invention does not obviate the need for an angle collimator as already proposed, but is preferably used in combination therewith.

The angle collimating device further reduces Skew rays and in practice is comprised of a fused fibre optic plate of the order of 5–10 mm thickness, which is mounted in advance of the camera input. Preferably it is made from glass fibres of relatively low numerical aperture (NA) typically of the order of 0.30. Such a device transmits wanted rays within the numerical aperture 0.22 of the bundle of fibres, but greatly reduces Skew rays that would otherwise be transmitted by the bundle.

By inserting the plate in front of the detector (eg before a camera input face plate) any tendency for spreading or cross-talk between the fibres and the detector is reduced.

It is important that the angle colimating device is placed after the interference filter since at that position it does not matter if the material from the which the collimating device is constructed itself produces any fluorescence. It is for example difficult to obtain a fused fibre optic plate of non-fluorescent material such as silica.

Reference has been made to Skew rays. In this connection the numerical aperture of a fibre is the cone-angle for the rays that are transferred with high efficiency by the fibre. In an ideal sense the condition only applies to meridional rays, ie those which pass along a plane including the axis of the fibre. The fibre is normally assumed to be a long cylinder.

In practice such rays are vanishingly few and the light transmitted by a fibre is normally considered to be all the rays within the same cone angle but entering the fibre at any point on the entry face of the fibre, since all these rays will also be transmitted with relatively high efficiency.

Skew rays are therefore those that enter at any point on the end face of the fibre but at an angle greater than $\sin^{-1}$ NA. The conditions for such rays to be transmitted are complicated and difficult to satisfy but in some situations up to half the rays transmitted by a fibre can be Skew rays.

In single channel assay systems, Skew rays are less of a problem since the light path in a single channel system can be highly collimated so as to more effectively remove them. The problem is more noticeable in multi-channel systems where there is insufficient space between the channels to allow optical collimating mechanisms to be accommodated.

In apparatus as aforesaid, the photosensitive detector is preferably a CCD, an ICCD, a cooled CCD, or photodiode or PMT array. Whatever device is chosen, it should have good spatial resolution after centroiding so as to be able to resolve individual fibre bundles in the final image to give minimal cross-talk between channels. A preferred spatial resolution is 10–20 microns.

The detector should have good quantum efficiency (QE).

Typically an ICCD will have a QE of 15% in the blue, falling to a few percent in the red.

A cooled CCD will have better QE rising to approximately 30% in the red.

When the optical system presenting light to the camera collects light from the sample via small diameter fibres (typically of the order of 100 microns diameter or less), and maintains this resolution throughout to the input of the photodetector, such as a CCD camera, and where the camera has a spatial resolution of the order of 10–20 microns, inspection of the area of the CCD array on which any light from one sample is incident, will allow light from individual fibres in the bundles conveying light from the sample to the camera to be identified. This for example enables light from a clump of cells in a sample to be observed, as distinct from separated individual cells, which can be useful.

Where this requires a focusing of the light passing through the interference filter region, a Grin lens or other device may be used, such as is described in our aforementioned PCT Application WO 98/01744.

It is to be understood that the present invention can be incorporated in all such systems, including those incorporating different detectors, and sub-well imaging using Grin lenses.

It is also to be understood that whereas the various aspects of the invention have so far been described in relation to well plates, each of the aspects of the invention is equally applicable to assay systems in which the samples occupy discrete areas of a membrane or gel or are distributed in the matrix of a sample support such as a wafer or chip of silicone or thin glass slide or sheet.

The invention will now be described by way of example with reference to the accompanying drawings, in which:

Figure 1:
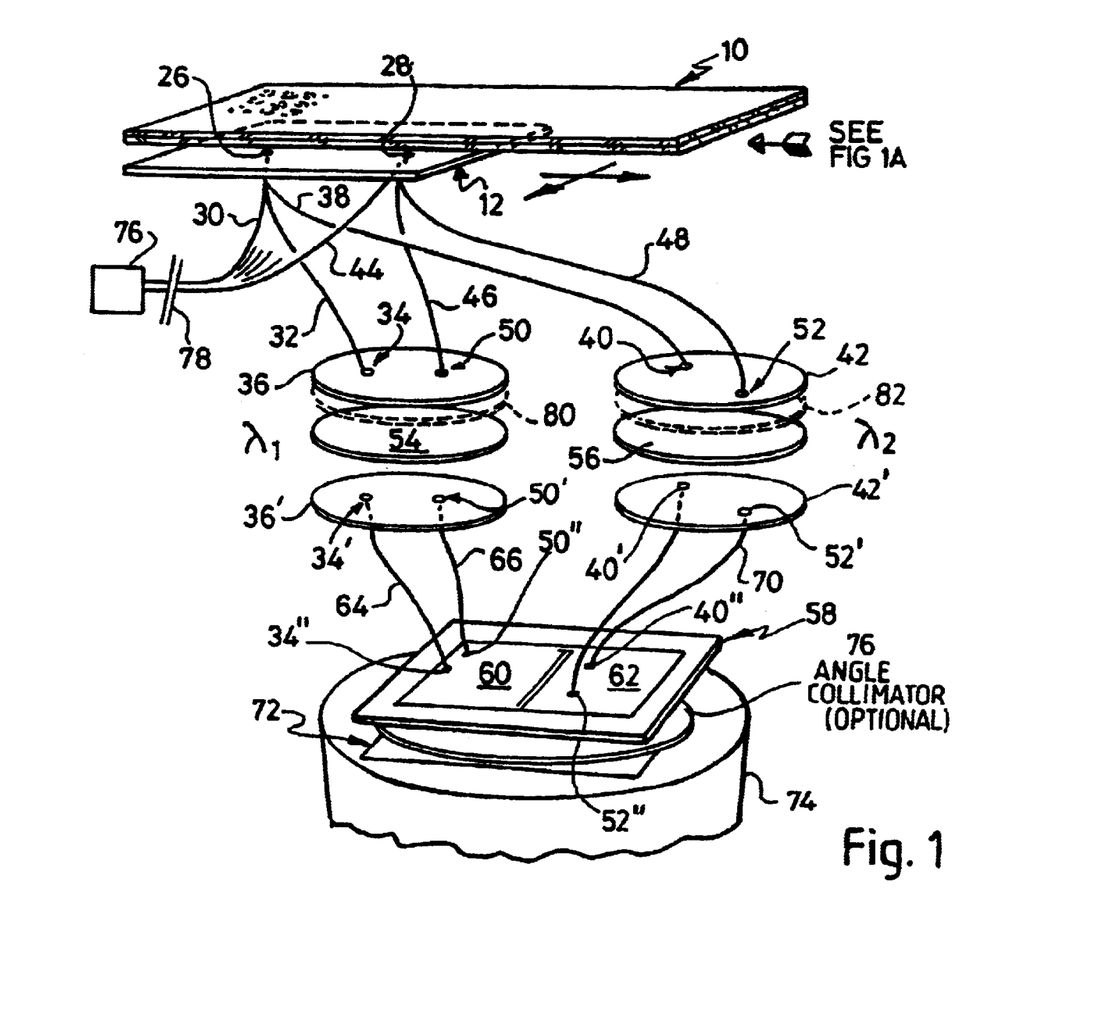
Figure 1A:
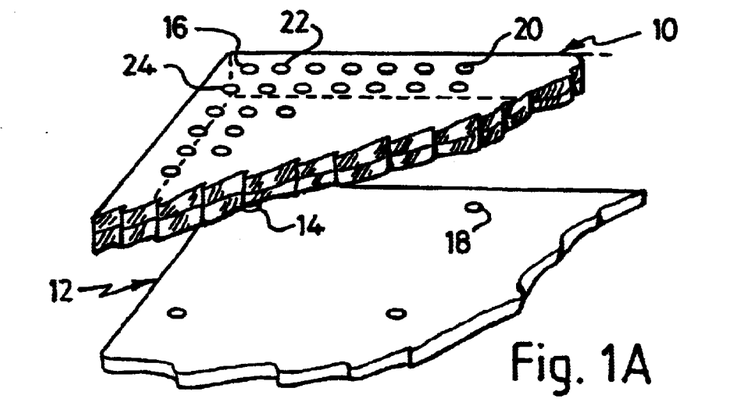

In FIGS. 1 and 1A, a well plate 10 is shown located above a presentation plate 12. The drawing is an exploded perspective view and the spacing implied by the drawing is an exaggeration of the actual spacing. In practice the presentation plate 12 will be very close to the underside of the well plate 10.

Well plates have tended to be constructed with either 96 wells typically arranged in 8 rows of 12 columns, but in recent years higher density plates have been constructed and a typical high density plate may contain, say, 36 times as many wells as the 96 well plate. However tie area of the plate is the same as is the basic matrix. The only difference in this case is that the well size has been decreased enabling six wells to be located along each row and six wells down each column in place of a single well in the original array. This means that instead of there being twelve wells along each row, there are now 72 and instead of there being eight rows, there are now 48 rows.

To take advantage of this and to simplify the indexing of a 96 aperture presentation plate, the latter is formed with openings which correspond in position to each of the original 96 wells of a 96 well plate, but equal in size to that of the wells in the 3456 well plate; This means that 96 of the 3456 wells can be inspected simultaneously by aligning the presentation plate 12 so that the first of the 96 apertures (14) coincides with the first of the 3456 wells, at position 60 in the well plate. This means that the second aperture 18 in the presentation plate aligns with the seventh well 20 along the first row, and so on.

Shifting the presentation plate 12 by a distance equal to the distance between apertures 16 and 22 (the next well in the first row adjacent 16) means that all of the 96 apertures in the presentation plate 12 will now be aligned with a new set of 96 of the wells in the well plate 10. By moving the presentation plate successively through six steps parallel to the rows containing wells 16, 22 and 20, and for each step six positions perpendicular to that row, in each case each movement corresponding to the distance between adjoining wells in the well plate measured perpendicular to the first row, (ie the distance between well 16 and well 24), so every one of the 3456 wells can be interrogated by 36 relative movements between the presentation plate and the well plate.

In practice, the well plate is moved relative to the presentation plate.

Each of the apertures such as 14 in the presentation plate 12 serves as a termination for a fibre bundle made up of 45 individual fibres. The fibres are shown terminating in two of the apertures for illustration only, one designated 26 and the other 28.

Each bundle of 45 fibres is made up of three groups of 15, one group such as 30 extending to an excitation light source, one group such as 32 conveying fluorescence light from a well aligned with the aperture 26 to an aperture 34 in a presentation disc 36. The third group of 15 fibres 38 extends to another opening 40 in a second presentation disc 42, for conveying fluorescence light to that other opening 40.

The three groups of 15 fibres making up the other illustrated bundle leading to and from aperture 28 are denoted by reference numerals 44, 46 and 48 respectively and these extend from the excitation light source in the case of group 44 and to two other apertures 50 and 52 respectively in the two presentation discs 36 and 42.

Each of the latter includes 96 apertures arranged regularly over the circular area of each disc, and similar discs 36' and 42' are aligned with the discs 36 and 42. Suitable optical filter discs 54 and 56 are sandwiched between discs 36 and 36', and discs 42 and 42'.

Apertures in the two discs 36, 36' (42, 42') are aligned on a one to one basis and fibres lead from each of the aligned apertures such as 34' in disc 36' to unique apertures in two groups of 96 apertures arranged in a rectilinear matrix in an output plate generally designated 58. The first such matrix is designated 60 and the second 62 and the fibres such as 64 from aperture 34' and 50' lead to apertures 34" and 50" in the matrix region 60 and the fibres 68 and 70 from apertures 40' and 52' in disc 42' lead to apertures such as 40" and 52" in matrix 62.

The two matrixes 60 and 62 together form a generally square outline which conforms approximately to the square aspect ratio of an input window illustrated at 72 in a camera 74.

Figure 2:
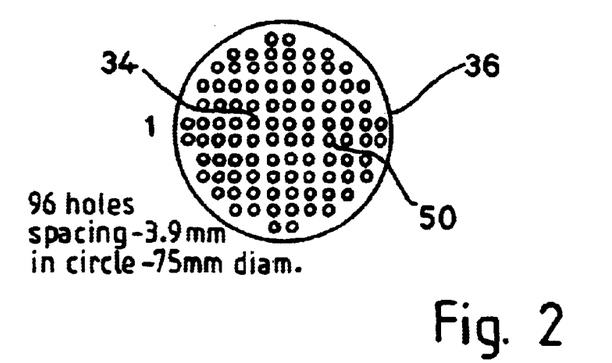

The excitation light source is denoted by reference numeral 76 and between it and the 96 groups of 15 fibres such as 30 and 44 is located a filter 78. The arrangement of the apertures such as 34 and 50 and 40 and 52 on each of the plates 36 and 42 is as shown in FIG. 2. Two of the openings are arbitrarily shown at 34 and 36.

Figure 3:
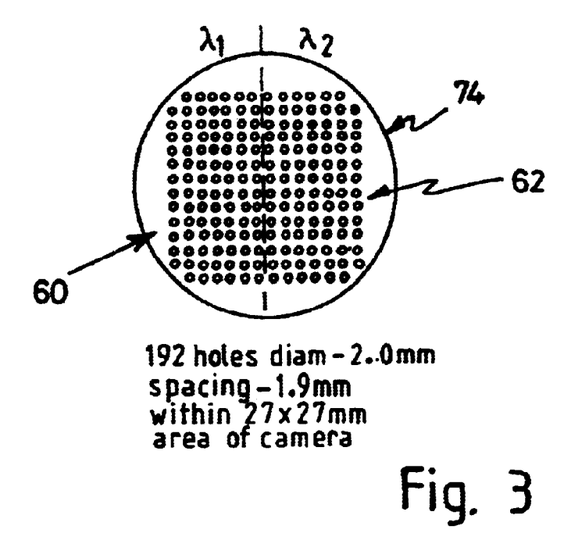

The arrangement of the two groups of 96 fibre ends in the two matrices 60 and 62 is shown in FIG. 3. The camera typically has a generally square aspect ratio and the arrangement of the 192 apertures making up the two matrices 60 and 62 makes the best use of the available generally square outline.

Figure 4:
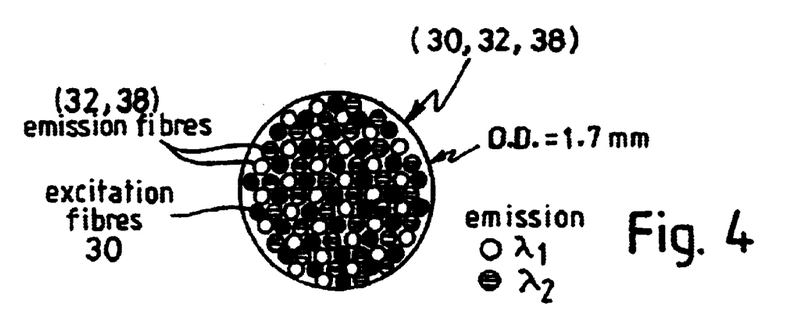

In accordance with a particularly preferred feature of the invention, the three groups of 15 fibres making up the bundle of fibres at each presentation plate aperture such as 16, is as shown in FIG. 4. Here the solid black fibre ends correspond to those in the excitation bundle 30, the clear circles correspond to those in the fibre bundle 32 leading to the first filter path containing filter 54, and the shaded circle corresponds to the fibres in the bundle 38 leading to the other wavelength selective path containing the second filter 56.

Each of the fibres illustrated in FIG. 4 is typically of the order of 100–200 microns diameter and comprises a pure silica core having a lower refractive index cladding, typically formed from doped silica cladding. Typically germanium is used as the dopant, although other materials may be employed. The resulting fibre has a numerical aperture of the order of 0.22.

Preferably the fibre also includes a coating around the cladding. The coating may for example be a polyamide or a material in the form of a thin layer such as obtained by metallisation of the surface of the cladding.

Materials for the core, cladding and any coating, preferably possess a very low tendency to fluoresce, so as to minimise the generation of unwanted light, which appears as background illumination, from which it may be difficult or impossible to distinguish light emitted by the array, due to similarity of wavelength and/or merely due to the relative amplitudes of the emitted and background light.

Experiments have shown that fibres as defined in the preceding paragraphs, permit a wide range of wavelength (including UV, visible and beyond into the infra red) to be accommodated, and low level background luminescence to result.

The numerical aperture can be increased by selecting different dopants and/or particular dopant properties, for the cladding material.

Using fibres of this size means that when bundled into a generally circular cross-section array the outside diameter of the bundle will be approximately 1.7 mm.

The particular arrangement of fibres shown in FIG. 4 has been found to be of considerable merit for ensuring high intensity of illumination from excitation light by ensuring that excitation fibre ends are uniformly distributed over the whole of the circular area of the fibre bundle and by uniformly arranging fibres leading to the two different wavelength selective paths equally uniformly throughout the remaining space, so an optimal excitation/collection characteristic is obtained for each well.

Although bundles of very tiny fibres are required between the presentation plate 12 and each of the presentation discs 36 and 42, the fibres leading from the discs 36' and 52' to the output plate 58 do not need to be made up of bundles of fibres but can be single fibres. Thus 64 for example may be a bundle of tiny fibres or a single fibre in each case having a typical outside diameter of 2 mm.

An angle collimating device 76 in the form of a thin plate may be located between the matrix array of fibre ends 34", 50" etc and the input window 72 of the camera 74.

The filters 54 and 56 are typically interference filters and preferably are interchangeable to allow different wavelengths to be selected.

Although the examples shown in the drawings are of a well plate, it is to be understood that the samples may be contained in any other supporting device such as a multi-well plate, multi-site membrane gel or wafer or chip of silicon or like material.

As indicated in FIG. 1 the area of presentation plate can be significantly less than the area of the well plate where there is a high ratio of samples to inspection apertures in the presentation plate. Also provided the arrangement and spacing and number of inspection apertures is suitable to align with groups of samples, and the one can be stepped relative to the other to obtain differing registrations, the aspect ratio and size of the sample support and the presentation plate can be quite different.

Additional filters 80, 82 for blocking Skew rays may also be incorporated, as shown in dashed line in FIG. 1, for the Purpose hereinbefore described.

INTERFERENCE FILTERS

As referred to herein, interference filters may comprise a large number of thin layers of dielectric materials, having differing refractive indices to produce constructive and destructive interference in transmitted light. Such filters can be designed to transmit a specific waveband only (a band pass filter) and can also be made to provide a very steep slope cut-on or cut-off at a particular wavelength, and to produce an edge filter.

Metallic layers may also be incorporated in such devices and in auxiliary blocking structures. Broadband interference filters usually contain a metallic layer.

Narrowband bandpass interference filters can be considered to be a Fabry-Perot interferometer, operating in the first order.

EXAMPLES OF BLOCKING AND INTERFERENCE FILTER COMBINATION

EXAMPLE 1

Fluorescein—A Green Fluorescence Assay

The peak excitation wavelength for Fluorescein in 485 nm and the peak of the emission is in the range 518–523 nm.

An interference filter is chosen whose peak transmission waveband is 525–530 nm and in accordance with the invention blocking filter is selected which attenuates wavelengths below 515 nm—such as a Schott OG 515 filter.

EXAMPLE 2

Coumarin—a Blue Fluorescence Assay

The peak excitation wavelength for Coumarin is 400 nm and the emission wavelength peaks in the range 455–460 nm.

An interference filter is chosen whose peak transmission wavelength is 460 nm and in accordance with the invention a blocking filter is selected which attenuates wavelengths below 455 nm—such as a Schott BG 455.

EXAMPLE 3

—Cy5—a Red Fluorescence Assay

The peak excitation wavelength for Cy5 is 649 nm and the peak emission occurs at 670 nm.

An interference filter is chosen whose peak transmission wavelength is 680 nm and in accordance with the invention a blocking filter is selected which attenuates wavelengths below 665 nm—such as a Schott RG 665.

EXAMPLE OF ENERGY TRANSFER ASSAY

Here no excitation radiation is required to stimulate emission.

One example of a Donor moiety is Luciferase which is a bioluminescent enzyme. An acceptor moiety could be a green fluorescent protein such as is derived from Renilla.

In this case the Donor emission wavelength is 480 nm and the Acceptor emission wavelength is 520 nm.

If an interference filter is employed having a peak transmission wavelength of 530 nm, then the blocking filter is preferably one having a cut-off wavelength of 515 nm—such as a Schott OG 515.

Where energy transfer occurs between donor and acceptor, the emission light to be measured is the acceptor emission at 520 nm.

When energy transfer does not take place, then there will be little or no emission from the acceptor but the donor will lose energy as light at its characteristic emission wavelength, of 480 nm in the above example.

In practice, both 520 nm and 480 nm will be monitored separately and the relative proportions of the wavelengths are measured.

Since the energy transfer process is not 100% efficient, the donor constituent will continue to emit light at its characteristic wavelength of 480 nm and the acceptor emissions will have to be measured against a background of donor emission. Thus in the above example 520 nm wavelength emissions will have to be measured against a background of donor emissions at 480 nm.

Examples of energy transfer assays, such as bioluminescence and chemiluminescence assays are to be found in "Chemiluminescence :Principles and Applications in Biology and Medicine" by A. K. Campbell. 1988. Published by Ellis Harwood Ltd of Chichester, England.

What is claimed is:

1. Apparatus for detecting luminescence in a sample, in which light emitted by the sample is collected for transmission photosensitive detector means by an optical fibre bundle the cross-sectional are of which corresponds to the are of the sample and one end of which is located close to but spaced from the sample for directly illuminating sample and collecting light emitted therefrom, selected ones of the fibres making up the bundle are separated from the remainder and extend to a light source to convey the light for direct illumination of the sample, and other fibres of the bundle serve to collect light emitted from the sample due to luminescence and provide a light path therefor to the photosensitive detector means, wherein the light collecting fibres are divided into a plurality of groups for conveying light to different regions of the detector means, thereby providing parallel light paths from the sample to the detector, and a wavelength selective filter is located in each of the said light paths to permit only selected wavelengths of light to reach the region of the detector means associated with each light path, and wherein the fibres in the bundle are arranged in a symmetrical pattern so that in the end face of the bundle presented to the sample, each sample illuminating fibre is surrounded by a ring of six light collecting fibres which, around the ring, successively constitute fibres appertaining to the respective groups of said light collecting fibres, whereby the sample illuminating fibres and the light collecting fibres are distributed uniformly over the area of the fibre bundle presented to the sample, and in which the apparatus is constructed to interrogate a well plate containing a plurality of wells, by investigating the luminescence characteristics of the plurality of wells at a time using a corresponding number of fibre bundles wherein two groups of collecting fibres from the plurality of fibre bundles are collected into two collection each of a corresponding number of fibre bundles, and each of the two collections is presented to one of two wavelength selective filters, each of which has a different wavelength filtering characteristic from the other, and two further bundles of optical fibres downstream of the filters separately collect and transfer light which is transmitted by the two filters, to two discrete regions of the detectors.

2. Apparatus according to claim 1, wherein the detector comprises a charge coupled device (CCD) array, a cooled CCD array, and intensified CCD (ICCD) array, or an array of photodiodes or PMT's.

3. Apparatus according to claim 1, wherein the wavelength selective filters are interference filters.

4. Apparatus according to claim 1, wherein one third of the fibres in the bundle can convey light to the sample, another third of the fibres collect and convey emitted radiation via a first wavelength selective filter to a first region of a detector, and the remaining third of the fibres collect and convey emitted radiation via a second wavelength selective filter to a second region of the detector.

5. Apparatus according to claim 1, constructed to interrogate a well plate containing a whole number multiple of 96 wells, by investigating the luminescence characteristics of 96 wells at a time using 96 fibre bundles, wherein two groups of light collecting fibres from the 96 fibre bundles are collated into two collections each of 96 fibre bundles.

6. Apparatus according to claim 5, wherein the said collections of fibres are arranged at their respective filters so as to optimally utilize the area of each filter.

7. Apparatus according to claim 1, wherein the detector has a non-circular aspect ratio and fibres leading from the wavelength selective filters to the detector are re-arranged so as to optimally occupy the area of the detector.

8. Apparatus according to claim 7, wherein the detector is generally square, and the fibres leading from the interference filter are re-arranged in two rectangular arrays which together make up a square corresponding to the detector.

9. Apparatus according to claim 5, in which each of the fibre optic bundles presented to a wall in the well plate is made up of 45 Ge-doped silica clad, silica fibres, each of a diameter in the range 100–200 micron, 15 of which are separated out as an excitation sub-bundle and combined with similar excitation sub-bundles of 15 from each of the 96 bundles, and the 96 excitation sub-bundles extend to a source of excitation radiation, and the remaining 30 fibres from each of the 96 bundles are divided into two further sub-bundles each of 15 fibres, to produce a total of 192 emission sub-bundles each of 15 fibres, 96 of which emission sub-bundles lead to discrete positions at the input of a first interference filter and the other 96 of which lead to discrete positions at the input of a second interference filter, which transmits light to a different wavelength from that transmitted by the first filter, and each of the two bundles downstream of the filters is comprised of 96 sub-bundles of fibres, each of which is arranged on a one to one basis with one of the 192 emission sub-bundles, at the input to the filter, and the 192 downstream sub-bundles are merged into an array having the same aspect ration as the detector.

10. Apparatus according to claim 1, wherein a blocking filter is provided in the light path to the detector and the characteristics of the blocking filter are such that light of a wavelength corresponding to that emitted by the sample due to the induced luminescence, is transmitted by the filter but unwanted light of different wavelengths is strongly attenuated thereby.

11. Apparatus according to claim 10, wherein the blocking filter is located in advance of a wavelength selective interference filter between it and the ends of optical fibres transmitting light from the sample to the interference filter, or between the interference filter and the detector.

12. Apparatus according to claim 10, wherein the blocking filter has a sharp cut-off between transmissions and attenuation, and a high attenuation of wavelengths below the cut-off point is selected to provide 50% attenuation at a wavelength closer to the wavelength of wanted radiation than to the wavelength of the nearest component of the unwanted radiation.

13. Apparatus according to claim 12, wherein fluorescence is produced by fluorescin and the blocking filter is Schott filter, Type OG515.

14. Apparatus according to claim 10, wherein the blocking filter is used in combination with an angle collimating device.

15. Apparatus according to claim 14, in which the angle collimating device is comprised of a fused fibre optic plate of the order of 5–10 mm thickness, which mounted in advance of the detector input.

16. Apparatus according to claim 15, wherein the angle collimating device is made from glass fibres of low numerical aperture of the order of 0.30.

17. Apparatus according to claim 1, wherein a GRIN lens is used to focus light passing through the wavelength selective filters.

18. Apparatus according to claim 10, wherein a first blocking filter is located in advance of the interference filter and a second blocking filter is located beyond the interference filter, between it and the detector.

* * * * *